United States Patent
Biltresse et al.

(10) Patent No.: US 12,391,772 B2
(45) Date of Patent: Aug. 19, 2025

(54) MODIFIED STARCHES FOR HOME CARE AND PERSONAL CARE

(71) Applicant: CARGILL, INCORPORATED, Wayzata, MN (US)

(72) Inventors: Stéphane Biltresse, Etterbeek (BE); Emmanuel Paul Jos Marie Everaert, Poissy (FR)

(73) Assignee: CARGILL, INCORPORATED, Wayzata, MN (US)

( * ) Notice: Subject to any disclaimer, the term of this patent is extended or adjusted under 35 U.S.C. 154(b) by 454 days.

(21) Appl. No.: 17/753,655

(22) PCT Filed: Sep. 10, 2020

(86) PCT No.: PCT/US2020/050110
§ 371 (c)(1),
(2) Date: Mar. 10, 2022

(87) PCT Pub. No.: WO2021/050671
PCT Pub. Date: Mar. 18, 2021

(65) Prior Publication Data
US 2024/0043570 A1    Feb. 8, 2024

Related U.S. Application Data

(60) Provisional application No. 62/899,204, filed on Sep. 12, 2019.

(51) Int. Cl.
*C08B 31/04* (2006.01)
*A61K 8/73* (2006.01)
*A61Q 5/02* (2006.01)
*A61Q 19/10* (2006.01)

(52) U.S. Cl.
CPC .............. *C08B 31/04* (2013.01); *A61K 8/732* (2013.01); *A61Q 5/02* (2013.01); *A61Q 19/10* (2013.01); *A61K 2800/30* (2013.01)

(58) Field of Classification Search
CPC .... C08B 31/04; A61K 8/732; A61K 2800/30; A61Q 5/02; A61Q 19/10
USPC .......................................................... 514/60
See application file for complete search history.

(56) References Cited

U.S. PATENT DOCUMENTS

| | | | |
|---|---|---|---|
| 4,011,392 A * | 3/1977 | Rudolph | ............... C09D 103/06 536/108 |
| 4,061,610 A | 12/1977 | Glowaky | |
| 5,321,132 A | 6/1994 | Billmers | |
| 5,470,841 A | 11/1995 | Forster | |
| 2011/0082290 A1 | 4/2011 | Gardner et al. | |
| 2012/0316099 A1 | 12/2012 | Fevola | |
| 2014/0030196 A1 | 1/2014 | Russell et al. | |
| 2016/0296454 A1* | 10/2016 | Bevinakatti | .............. A61Q 5/06 |

FOREIGN PATENT DOCUMENTS

| | | |
|---|---|---|
| CN | 102079821 A | 6/2011 |
| EP | 0761691 B1 | 1/2002 |
| EP | 1685162 B1 | 5/2014 |
| EP | 1964969 B1 | 7/2018 |
| JP | 2017-125124 A | 7/2017 |
| WO | 2018213393 A1 | 11/2018 |

OTHER PUBLICATIONS

O.B. Wurzburg, "Converted Starches", Ed. Modified Starches: Properties and Uses, CRC Press, Florida, 1987; ISBN 0-8493-5964-3.

Rupendra Mukerjea et al., "Determination of the maximum water solubility of eight native starches and the solubility of their acidic-methanol and -ethanol modified analogues", Carbohydrate Research, 342 (1), Jan. 15, 2007, pp. 103-110.

\* cited by examiner

*Primary Examiner* — Yih-Horng Shiao

(57) ABSTRACT

The present application provides for novel anhydride substituted starches and their use in personal and home care products. The natural based starches disclosed are useful for the replacement of chemical surfactants in personal and home care products. The starches demonstrate the unique ability to create and maintain desired properties in these products. The anhydride substituted starches are particularly useful in replicating the foaming properties of standard chemical surfactants.

19 Claims, No Drawings

MODIFIED STARCHES FOR HOME CARE AND PERSONAL CARE

CROSS-REFERENCE TO RELATED APPLICATIONS

This application is a national phase application of PCT Application No. PCT/US2020/050110, Sep. 10, 2020, which claims the benefit of U.S. Provisional Application No. 62/899,204, filed Sep. 12, 2019, each of which is incorporated by reference herein in its entirety.

FIELD OF INVENTION

The present invention relates to the production of anhydride modified starches for use in home care and personal care applications. Specifically, the use of highly anhydride substituted starches allows for the manufacturing of compositions that lower or no other surfactants while maintaining desirable sensory characteristics like foaming.

BACKGROUND

There is a lack of naturally sourced solutions in the personal care and home care markets that are capable of replacing currently used chemical surfactants. Surfactants are compounds that lower the surface tension (or interfacial tension) between two liquids, between a gas and a liquid, or between a liquid and a solid. Surfactants may act as detergents, wetting agents, emulsifiers, foaming agents, and dispersants. Surfactants are usually organic compounds that are amphiphilic, meaning they contain both hydrophobic groups (their tails) and hydrophilic groups (their heads). Therefore, a surfactant contains both a water-insoluble (or oil-soluble) component and a water-soluble component. Surfactants will diffuse in water and adsorb at interfaces between air and water or at the interface between oil and water, in the case where water is mixed with oil. The water-insoluble hydrophobic group may extend out of the bulk water phase, into the air or into the oil phase, while the water-soluble head group remains in the water phase. World production of surfactants is estimated at 15 milliontons/y, of which about half are soaps. Other surfactants produced on a particularly large scale are linear alkylbenzene sulfonates, lignin sulfonates, fatty alcohol ethoxylates, and alkylphenol ethoxylates. Personal care and home care products often contain a surfactant to aid in wetting and/or foaming. The present disclosure provides an alternative sources of naturally-based highly effective replacements for surfactants in personal and home care products.

SUMMARY OF INVENTION

The present disclosure provides: An anhydride modified starch wherein the anhydride modified starch has (i) a degree of substitution between 10% and 80% and (ii) was prepared from a base starch having an average molecular weight of between 15,000 and 200,000 g/mol.

Preferably the anhydride modified starch that is a nOSA modified starch.

The anhydride modified starch preferably comprises a degree of substitution between 0.2 and 0.5.

The anhydride modified starch is preferably prepared from a base starch having average molecular weight of between 15,000 and 50,000 g/mol.

The present disclosure also provides: A personal care or home care formulations comprising an anhydride modified starch wherein the anhydride modified starch has (i) a degree of substitution between 10% and 80% and (ii) was prepared from a base starch having an average molecular weight of between 15,000 and 200,000 g/mol.

Preferred personal care formulations are selected from the group consisting of shampoo, sulphate free shampoo, hair conditioner, hair leave on, body wash, skin cleanser, hair cleanser, bar soap, toothpaste, and mouthwash.

Preferably the personal care formulation comprise an anhydride modified starch that is a nOSA modified starch.

The personal care formulations preferably comprise an anhydride modified starch with a degree of substitution between 0.2 and 0.5. This degree of substitution is much higher than that allowed in food use nOSA starches where the upper regulatory limit is typically 0.03 or 3%. The nOSA starch of the present disclosure can have a 10 for, or more, greater degree of substitution than food starches.

The personal care formulations are preferably prepared from a base starch having average molecular weight of between 15,000 and 50,000 g/mol.

The personal care formulation preferably comprises between 0.1% and 50%, 1% to 25%, or 1% to 15% of anhydride modified starch by weight.

DETAILED DESCRIPTION

Explanations of abbreviations and terms used in this disclosure are provided to assist in comprehending and practicing the invention.

All ratios of formulation components refer to percentage by weight (wt %), unless otherwise specified.

All parameter ranges disclosed include the end-points and all values in between, unless otherwise specified.

Representative features are set out in the following description, which stand alone or may be combined, in any combination, with one or more features disclosed elsewhere in the description and/or drawings of the specification.

When used in this specification and claims, the terms "comprises" and "comprising" and variations thereof mean that the specified features, steps or integers are included. The terms are not to be interpreted to exclude the presence of other features, steps or components.

When used in this specification and claims the term "Surfactant(s)" means an organic compounds with a molecular weight of less than 1000 g/mol, that are amphiphilic, meaning they contain both hydrophobic groups and hydrophilic groups. Surfactants may be anionic, cationic, non-ionic or amphoteric; and mixtures thereof. Examples of surfactants include but are not limited to the following: coco glucoside, cocamidopropyl betaine, coco betaine, sodium cocoyl isethionate, sodium cocoyl methyl isethionate, lauryl ether carboxylic acid, lauryl betaine, sodium cocoamphoacetate, sodium laurylamphoacetate, lauryl hydroxy sultaine, lauyl taurate, cocyl taurate, cocyl methyl taurate, coco hydroxy sultaine, lauryl aminopropyl hydroxy sultaine, coco aminopropyl hydroxy sultaine, sodium lauryl sulphate, sodium lauryl ether sulphate (n)EO, (where n is from 1 to 5), sodium ($C_{12-13}$) pareth sulphate, ammonium lauryl sulphate, ammonium lauryl ether sulphate(n)EO, (where n is from 1 to 5), and mixtures thereof.

Starches

Starch is a polymeric carbohydrate consisting of a large number of glucose units joined by glycosidic bonds. This polysaccharide is produced by most green plants as energy storage. It is the most common carbohydrate in human diets and is contained in large amounts in staple foods. Starches useful in the present disclosure can come from any plant source including but not limited to: potatoes, wheat, maize (corn), rice, tapioca, *quinoa*, cassava, and the like. Pure starch is a white, tasteless and odorless powder that is insoluble in cold water or alcohol. It consists of two types of molecules: the linear and helical amylose and the branched amylopectin. Depending on the plant, starch generally contains 1 to 25% amylose and 75 to 99% amylopectin by weight. When it is isolated directly from the plant source it is most often referred to as "native starch". Native starch requires heat to thicken or gelatinize. When a starch is pre-cooked, it can then be used to thicken instantly in cold water. This is referred to as a pregelatinized starch.

Native starch can be hydrolyzed into simpler carbohydrates by temperature, acids, various enzymes, or a combination of the three. The resulting fragments are known as dextrins or hydrolyzed starch. The extent of conversion is typically quantified by dextrose equivalent (DE), which is roughly the fraction of the glycosidic bonds in starch that have been broken. For example, maltodextrin is a lightly hydrolyzed (DE 4-20 or 10-20) starch product used as a bland-tasting filler and thickener. Various glucose syrups (DE 30-70), also called corn syrups in the US, are a type of hydrolyzed starch that are viscous solutions used as sweeteners and thickeners in many kinds of processed foods. Dextrose (DE 100), commercial glucose, is prepared by the complete hydrolysis of starch.

The starch may also be a cyclodextrin. Cyclodextrins are a well-known family of cyclic oligosaccharides, consisting of a macrocyclic ring of glucose subunits joined by $\alpha$-1,4 glycosidic bonds. Cyclodextrins are produced from starch by enzymatic conversion. They are used in food, pharmaceutical, drug delivery, and chemical industries, as well as agriculture and environmental engineering. Cyclodextrins are composed of 5 or more $\alpha$-D-glucopyranoside units linked 1→4, as in amylose (a fragment of starch). The largest cyclodextrin contains 32 1,4-anhydroglucopyranoside units, while as a poorly characterized mixture, at least 150-membered cyclic oligosaccharides are also known. Typical cyclodextrins contain a number of glucose monomers ranging from six to eight units in a ring, creating a cone shape including: 1) $\alpha$ (alpha)-cyclodextrin: 6 glucose subunits; 2) $\beta$ (beta)-cyclodextrin: 7 glucose subunits; and 3) $\gamma$ (gamma)-cyclodextrin: 8 glucose subunits.

The starch of the present disclosure may also be characterized by the average molecular weight of the glucose chains in the starch sample. Average molecular weight (hereinafter referred to as "MW") may be determined by methods know in the art and as described below and may be represented in g/mol or Daltons. Aspects of the present invention include base starches that have an average molecular weight of less than 200,000 g/mol; or between 100-200,000 g/mol, or between 50,000-200,000 g/mol, between 15,000-200,000 g/mol, between 15,000-200,000 g/mol, between 15,000-100,000 g/mol, or between 15,000-50,000 g/mol.

Preferably the modified-starch has a polydispersity index (PDI) of from 2 to 25 and more preferably from 4 to 20. The PDI is a well-known and understood measure of the distribution of molecular mass in a given sample. The PDI can be calculated by division of Mw by the number average molecular weight (Mn). It indicates the distribution of individual molecular masses in a batch of samples. The PDI has a value which is always one or more (i.e Mw≥Mn), but as the samples approach uniformity, PDI approaches the unity (PDI→1).

A modified starch has a structure that has been altered from its native state, resulting in modification of one or more of its chemical or physical properties. Starches may be modified, for example, by enzymes, oxidation or, substitution with various compounds. For example, starches can be modified to increase stability against heat, acids, or freezing, improve texture, increase or decrease viscosity, increase or decrease gelatinization times, and/or increase or decrease solubility, among others. Modified starches may be partially or completely degraded into shorter chains or glucose molecules. Amylopectin may be debranched. In one example, modified starches are cross-linked for example to improve stability. Starches that are modified by substitution have a different chemical composition.

The base-starch used as the base material for obtaining the modified-starch utilized in the present invention can be sourced from any starch containing sources (hereinafter base material) including for example corn, wheat, potato, tapioca, barley, pea, dent corn, waxy maize, sago, rice, sorghum and high amylose starch, i.e., starch having at least 15% and more particularly at least 02% amylose content, such as high amylose corn. Starch flours may also be used.

The base-starch may be chemically converted, enzymatically converted, or converted by heat treatment or by physical treatment. The term "chemically converted" or "chemical conversion" include, but is not limited to crosslinking, modification with blocking groups to inhibit retrogradation, modification by the addition of lipophilic groups, acetylated starches, hydroxyethylated and hydroxypropylated starches, inorganically esterified starches, cationic, anionic and oxidized starches, zwitterionic starches and combinations thereof. By an "enzymatically converted starch" is herein understood starches converted by enzymes. Heat treatment includes for example pre-gelatinization. The base-starch may have a granular state, which is preferred, or a non-granular state, i.e. the granular state of the starch has been disrupted by physical, thermal, chemical or enzymatic treatment. Preferred base materials include converted or non-converted starches originating from corn, high amylose corn, wheat, potato, tapioca, waxy maize, sago or rice. Preferred base materials to manufacture the base-starches are those chosen from the group consisting of corn starch, wheat starch and potato starch. Most preferred base materials are corn starch and wheat starch.

Preferably, the base-starch is chosen from the group consisting of maltodextrins; pyrodextrins; dextrins such as those prepared by hydrolytic action of acid and/or heat or by the action of enzymes; degraded starches such as for example fluidity or thin boiled starches prepared for example by enzyme conversion, thermal treatment or acid hydrolysis; oxidized starches prepared by treatment with oxidants such as sodium hypochlorite, peroxides and persulfates; and derivatized starches such as cationic, anionic, amphoteric, non-ionic and cross-linked. Any base material can be used for producing these base-starches, such as for example those mentioned above.

For clarity, by dextrin is herein understood a depolymerized starch prepared by hydrolytic action of acid and/or heat or by the action of enzymes. Preferably, the dextrin used in accordance with the present invention is prepared by depolymerizing the starch with a dry or semi-dry (moisture below 10 wt %) thermal treatment. An example of such treatment is disclosed in EP 1 685 162 A1.

Preferably, the base-starch is chosen from the group consisting of maltodextrins, dextrins, thin boiled starches and oxidized starches, said base-starch being produced from a base material chosen from the group consisting of non-converted corn starch, non-converted wheat starch and non-converted potato starch.

More preferably, the base-starch is chosen from the group consisting of maltodextrins, dextrins, thin boiled starches and oxidized starches, said base-starch being produced from a base material those chosen from the group consisting of non-converted corn starch and non-converted wheat starch.

The modified-starch used in accordance with the invention is obtained reacting the base-starch with at least an anhydride of a polyacid, hereinafter for simplicity being referred as "the anhydride".

Preferably, the anhydride is a cyclic anhydride. More preferably, the anhydride is chosen from the group consisting of maleic and succinic anhydrides. Most preferred succinic anhydrides are those chosen from the group consisting of (alkyl-, alkenyl-, aralkyl- or aralkenyl-) succinic anhydrides. Even more preferably, the anhydride is chosen from the group consisting of alkyl-succinic anhydrides and alkenyl-succinic anhydrides, wherein the alkyl or alkenyl group has from 0 to 22 carbon atoms, most preferably from 0 to 10 carbon atoms. Most preferably, the anhydride is an n-octenyl succiate anhydride (nOSA).

It is known in the art how to manufacture an anhydride-modified-starch, e.g. from U.S. Pat. No. 5,321,132; EP 0 761 691 or from "Converted Starches", O. B. Wurzburg, Ed. Modified Starches: Properties and Uses, CRC Press, Florida, 1987; ISBN 0-8493-5964-3; See pages 136&137. Preferably, the method to prepare the modified-starch used in accordance with the invention comprises the steps of (i) providing a mixture by pre-dispersing or intimately contacting by mixing at low acidic pH the anhydride with the base-starch to be modified; and (ii) bringing the mixture to reaction conditions.

Preferably, the anhydride modified-starch is prepared in accordance with a method wherein the base-starch is reacted with the anhydride in an aqueous system, said method comprising the steps of:

a) Preparing a solution, partial solution, or slurry of the base-starch in water at a pH of at most 9.0, more preferably between 1.0 and 9.0;

b) Maintaining and if necessary adjusting the pH of said slurry to between 5.0 and 9.0, more preferably between 7.0 and 9.0, most preferably between 8.0 and 9.0 while adding the anhydride to the slurry, said anhydride having a formula:

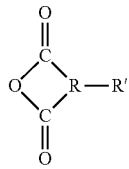

where R is a dimethylene or trimethylene group and R' is a hydrocarbon group having 0 to 20 carbon atoms, more preferably having 0 to 10 carbon atoms;

c) Optionally, intimately contacting the base-starch and the anhydride by mixing to preferable form a stable dispersion, wherein by stable dispersion is herein understood that the dispersion does not show signs of separation for at least the time until said dispersion is further processed;

wherein at step (b), the pH is maintained within the desire range by adding alkali material, e.g. by vigorous stirring, to the slurry and wherein said alkali material is added while adding the anhydride.

The obtained modified-starch has the formula:

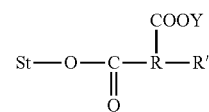

where St is the base-starch utilized at step (a), R is a dimethylene or trimethylene group, R' is a hydrocarbon group having 0 to 12 carbons, and Y is H, alkali metal, alkaline earth metal or ammonium.

The anhydride used in the method of this invention has the following structural formula:

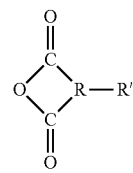

where R represents a dimethylene or trimethylene group and R' is a substituent hydrocarbon group having 0 to 20 carbons, more preferably 0 to 12, and most preferably 0 to 8 carbons.

The hydrocarbon or hydrophobic substituent group R' may be alkyl, alkenyl, aralkyl or aralkenyl with alkyl and alkenyl being preferred. R' may be joined to the anhydride moiety R through a carbon-to-carbon bond (as in alkenyl succinic anhydride) or through two carbon-to-carbon bonds (as in the adduct of maleic anhydride with methyl pentadiene, or as in the cyclo-paraffinic cyclo-dicarboxylic acid anhydrides such as cyclo hexane 1,2-dicarboxylic acid anhydride), or may be linked through an ether or ester linkage (as in octyloxy succinic anhydride or in capryloxy succinic anhydride).

The pH at step a) of the method described above, must be at most 9.0, preferably acidic. Preferably, said pH is from 1.0 to 9.0, more preferably from 3.0 to 8.0, most preferably from 5.0 to 7.0. By slurry is herein understood a solution or dispersion of starch in water.

The pH at step b) of the method described above is preferably between 7.5 and 9.0, most preferably between 8.0 and 9.0. The inventors observed that under these conditions, not only that the efficiency of the method increased, but also the properties of the modified-starch were optimized.

Preferably, the composition of the invention contains an anhydride modified starch, said anhydride modified starch being modified with an anhydride of a polyacid, said anhydride being preferably chosen from the group consisting of maleic and succinic anhydrides, more preferably from the group consisting of (alkyl-, alkenyl-, aralkyl- or aralkenyl-) succinic anhydrides. More preferably the succinic anhydride has a chain length between 3 and 22 carbons or specifically a chain length of 8, 10, 12, 14, 16, 18 or combinations thereof. Most preferably said anhydride is n-octenyl succinic anhydride.

Anhydride modified starches can be characterized by the degree of substitution of alkyl groups. The degree of substitution is abbreviated at "DS". For example, it is preferred for the anhydride modified starches of the present disclosure to have a DS of between 0.1 and 0.8 or between 10% and 80% substituted. Other aspects of this disclosure provide for anhydride modified starches to have a DS of between 0.2 and 0.7 or between 20% and 70% substituted. Other aspects of this disclosure provide for anhydride modified starches to have a DS of between 0.2 and 0.4 or between 20% and 40% substituted.

A nOSA starch is a modified starch that has been partially substituted by reaction with n-octenyl succinic anhydride. nOSA starches can also be characterized by the degree of substitution of the n-octenyl succinic groups. The degree of substitution is abbreviated at "DS". It is a well understood and used nomenclature by those of skill in the art. For example, food grade approved nOSA starches are required to have a DS of 0.01 to 0.03. This means that between 1%-3% of potential loci have been substituted by n-octenyl succinic groups. Therefore, the maximum allowable DS for nOSA starch for food use is 0.03 or 3% substitution.

Effective nOSA starches of the present disclosure have a DS much higher than that allowed for food use and can be prepared from any base starch described herein.

A hydroxypropylated starch (HP starch) is another example of a modified starch that has been functionalized by hydroxypropylation. Such hydroxypropylated starches are well known in the art and are "E-coded" under the designation 1400 in the International System for Food Additives (INS). Preferred hydroxypropylated starches of the present invention include C*HiForm 12748 commercially available from Cargill Incorporated.

Examples of the present disclosure can replace surfactants in home care and personal care products. These products often use complex surfactant systems to achieve their desired properties. Such formulations can include anionic surfactants, cationic surfactants, and, or amphoteric surfactants. Anionic surfactants have a negative charge on their hydrophilic end. The negative charge helps the surfactant molecules lift and suspend soils in micelles. Because they are able to attack a broad range of soils, anionic surfactants are used frequently in soaps and detergents. Anionic surfactants create a lot of foam when mixed. While anionic surfactants are excellent for lifting and suspending particulate soils, they are not as good at emulsifying oily soils. Sulfates, sulfonates, and gluconates are examples of anionic surfactants. Cationic surfactants have a positive charge on their hydrophilic end. The positive charge makes them useful in anti-static products, like fabric softeners. Cationic surfactants can also serve as antimicrobial agents, so they are often used in disinfectants. Cationic and nonionic surfactants, however, are compatible. Examples of some common cationic surfactants include alkyl ammonium chlorides. Amphoteric surfactants have a dual charge on their hydrophilic end, both positive and negative. The dual charges cancel each other out creating a net charge of zero, referred to as zwitterionic. The pH of any given solution will determine how the amphoteric surfactants react. In acidic solutions, the amphoteric surfactants become positively charged and behave similarly to cationic surfactants. In alkaline solutions, they develop a negative charge, similar to anionic surfactants. Amphoteric surfactants are often used in personal care products such as shampoos and cosmetics. Examples of some frequently used amphoteric surfactants are betaines and amino oxides.

As seen if the examples below, the anhydride modified starches of the present disclosure can be used to replace some, or all, of the cationic, anionic, or amphoteric surfactants in personal care products. Therefore, these modified starches create unique flexibility for the formulator of personal care products. It is even possible to create surfactant-free personal care products.

Topical Formulation

The emulsion provided herein is useful in the manufacture of topical formulations such as personal care products or cosmetics. The inventors unexpectedly found that formulations comprising a specific nOSA starch have numerous desirable characteristics as explained further below.

In one aspect, the present invention is a topical formulation comprising an anhydride modified starch as described herein. As used herein, the term "topical formulation" refers to a formulation that may be applied directly to a part of the body. The term "formulation" is used herein to denote compositions of various ingredients in various weight ranges, in accordance with the present disclosure for use in personal or home care.

"Personal care" means and comprises any cosmetic, hygienic, toiletry and topical care products including, without limitation, leave-on products (i.e., products that are left on keratinous substrates after application); rinse-off products (i.e., products that are washed or rinsed from keratinous substrates during or within a few minutes of application); shampoos; hair curling and hair straightening products; combing or detangling creams, hair style maintaining and hair conditioning products (either concentrated masks or more standard formulations; whether rinse-off or leave-on); lotions and creams for nails, hands, feet, face, scalp and/or body; hair dye; face and body makeup; nail care products; astringents; deodorants; antiperspirants; anti-acne; antiaging; depilatories; colognes and perfumes; skin protective creams and lotions (such as sunscreens); skin and body cleansers; skin conditioners; skin toners; skin firming compositions; skin tanning and lightening compositions; liquid soaps; bar soaps; bath products; shaving products; and oral hygiene products (such as toothpastes, oral suspensions, and mouth care products).

The anhydride modified starches disclosed herein are particularly useful in reducing or replacing the various surfactants utilized in shampoo and conditioner formulations. They are capable of replacing individually or collectively the anionic, neutral, or amphoteric surfactants typically used in these formulations.

The texture of such personal care formulations is not limited and may be, without limitation, a liquid, gel, spray, emulsion (such as lotions and creams), shampoo, pomade, foam, tablet, stick (such as lip care products), makeup, suppositories, among others, any of which can be applied to the skin or hair or hale and which typically are designed to remain in contact therewith until removed, such as by rinsing with water or washing with shampoo or soap. Other forms could be gels that can be soft, stiff, or squeezable. Sprays can be non-pressurized aerosols delivered from manually pumped finger-actuated sprayers or can be pressurized aerosols such as mousse, spray, or foam forming formulation, where a chemical or gaseous propellant is used.

Formulations prepared using the anhydride modified starch disclosed herein have a white or pale white color that is generally considered to be aesthetically appealing. In some cases, the formulations of this disclosure may be further processed to make a colored end product. In such cases, the white color is beneficial because it will show up the additional pigment without influencing the final color.

Formulations containing the anhydride modified starch of the present disclosure may optionally contain additional ingredients to tailor the viscosity to the needs of the particular application. A skilled artisan will readily appreciate the range of additives available to suit this purpose including but not limited to the following: *sclerotium* gum, xanthan gum, carrageenan, gellan gum, native starches, modified starches, sodium starch octenylsuccinate, aluminium starch succinate, hydroxypropyl starch phosphate, pectin, calcium citrate, salt(s) NaCl, KCl, acrylate polymers, acrylate based copolymers, carbomers, cellulose, citrus fibres and derivatives, hydroxy ethyl cellulose, carboxy methyl cellulose, polyols such as sorbitol, and mixtures thereof. These additives may be utilized to add texture, viscosity, or structure to the formulations. A skilled artisan would appreciate that they may be present in various concentrations depending on the needs of the particular formulation and may even be the predominant element of a particular formulation. Additional texturizers may, or may not be used, in formulations including the anhydride modified starches disclosed herein and will depend on the needs of the formulation and objective of the product being prepared. It may be desired to add additional texturizers to aid in viscosity when the anhydride modified starch disclosed herein are used in shampoos or in hair conditioning formulations.

Formulations containing the anhydride modified starch of the present disclosure may optionally contain at least one further ingredient chosen from the group consisting of preservative, salt, vitamin, emulsifier, texturiser, nutrient, micronutrient, sugar, protein, polysaccharide, polyol, glucose, sucrose, glycerol, sorbitol, pH adjusters, emollients, dyes, pigments, skin actives, waxes, or silicones.

Formulations containing the anhydride modified starch of the present disclosure may have a wide range of pH values. Aspects of this disclosure include formulations having pH between 3-11, or between 4-8, or between 4-7.

Formulations of the present disclosure can contain any useful amount of the anhydride modified starch of the present disclosure. Formulations will preferably contain between 1-50% 1-30% 2-20%, or 3-15% by weight modified starch in the final formulations.

Methods of Measurement

Mw, Mn of a modified-starch sample was determine as follows: The sample was dissolved in DMSO-water 90-10 v:v at about 2 wt % dry substance. The GPC system used was Waters 600 controller with Waters 717 puls autosampler. Detector: water 2414 Refractive index detector. The RI detector system was calibrated with a set of *Pullulans* of known molecular weight. Also, a reference starch having a peak molecular weight of $20.10^6$ (measured by static Light Scattering), and a five units dextrose linear polymer (DP 5) was injected. For each calibrant, the logarithm of the molecular weight is plotted against the retention time. After completion of a run, the data processing system fitted the baseline, and cut the area comprised between the baseline and the chromatogram into a large number of small slices. The area of each slice was recorded, and the molecular weight corresponding to each slice was derived from the calibration curve. Using those data, the data processing system calculated the molecular weights. Column: Shodex KS-806+ Shodex KS-804+Shodex KS-802 (all sodium form) in series, at 75° C. Eluent: NaOH 0.05 M in HPLC grade water, filtered through 0.45 um filter, degassed and maintained at about 70° C. Flow: 1.0 ml/min. Injection: 20 µl. Detection: Differential refractive index. Data acquisition: Atlas from Thermo. Data processing; Caliber (GPC package from Polymer Labs).

DE: was determined according to the well-known Lane and Eynon method using the following apparatus. Titrating Assembly: a ring support was mounted on a ringstand 1-2 ins. above a gas burner and a second ring 6-7 ins. above the first. A 6 in. open wire gauze was placed on the lower ring to support a 200 mL Erlenmeyer flask and a 4 in. watch glass with center hole on the upper ring to deflect heat. A 25 mL buret was attached to the ringstand so that the tip just passes through the watch glass centered above the flask (funnel top buret with diagonal TEFLON Plug, KIMAX No. 17055F recommended). An indirectly lighted white surface was placed behind the assembly for observing the end point. The following reagents were used: (i) Fehling's Solution: (A) 34.64 g of reagent grade crystalline copper sulfate pentahydrate ($CuSO_4 \cdot 5H_2O$) was dissolved in purified water and diluted to 500 mL volume. (B) 173 g of reagent grade potassium sodium tartrate tetrahydrate ($KNaC_4H_4O_6 \cdot 4H_2O$) and 50 g of reagent grade sodium hydroxide (NaOH) were dissolved in purified water and diluted to 500 mL volume. A quantity of (A) was mixed with an equal quantity of (B). (C) A quantity of National Institute of Standards and Technology (NIST) dextrose was dried in a vacuum oven at 70° C. for 4 hrs. 3.000 g thereof was dissolved in purified water, diluted to 500 mL volume and mixed thoroughly. 25.0 mL of mixed Fehling's Solution was pipetted into a 200 mL Erlenmeyer flask that contains a few glass beads, and titrated with the standard dextrose solution as directed under procedure. The concentration of Fehling's Solution A was adjusted by dilution or addition of copper sulfate so that the titration requires 20.0 mL of the 0.6% standard dextrose solution. (ii) Methylene Blue Indicator: 1% aqueous solution. PROCEDURE: an amount of sample was weighed accurately such that after dilution the solution contains about 0.6% reducing sugars. The sample was transferred quantitatively to a 500 mL volumetric flask with the aid of hot water, cool to room temperature, diluted to volume and mixed thoroughly. 25.0 mL of standardized mixed Fehling's Solution was pipetted into a 200 mL Erlenmeyer flask and a few glass beads were added. The sample solution was added by means of the buret to within 0.5 mL of the anticipated end point (determined by preliminary titration). Immediately the flask was placed on the wire gauze of the titration assembly, and the burner adjusted so that the boiling point will be reached in about 2 mins. The solution was brought to boil and boiled gently for 2 mins. As boiling continues, 2 drops of methylene blue indicator were added and the titration was completed within 1 min. by adding sample solution dropwise or in small increments until the blue color disappears. The dry substance concentration of the sample was determined.

Calculation:
% Reducing Sugars (as is calc. as dextrose)=[(500 mL) (0.1200)(100)]/[Sample Titer, mL)(Sample Wt, g)]. DE=[(% Reducing Sugars)(100)]/(% Dry Substance Content). See http://corn.org/wp-content/uploads/2009/12/DEXTR.02.pdf and notes therein.

DS: was calculated from the consumption of reagent and caustic (in moles) during reaction: DS=2 [M anhydride]−[M NaOH]/[M starch or dextrin] wherein M [Starch or dextrin] =weight starch used (g)/162 g (=Mw anhdroglucose unit).

pH of a modified-starch was determined as follows: a droplet of a solution consisting of a pH indicator and up to 100 wt % Millipore water was placed on a surface of a sample (usually a coating) consisting of the modified-starch. The used pH indicators and their respective amounts are well known in the art. For example, bromocresol green solution (0.04%) was used and showed a blue colour when the coating was under neutral to alkaline conditions. After the acidic treatment, the blue colour disappeared and may become slightly yellowish depending on the colour of the base paper. The local surface pH was determined as at most 2.5-3, according to the table.

Solubility in mg/nL of modified-starch can be determined according to the methodology described in the experimental section of Rupendra Mukerjea et al., Carbohydrate Res. 342 (2007) 103-110.

Solubility in wt % of modified-starches: was determined as indicated in EP 1 964 969 A1—see "Methods" section therein.

Dry substance content (DS) is measured according to formula: DSC (%)=100%−MC (%).

Viscosity: Brookfield (RV, 100 rpm, 25° C., spindle adapted to the viscosity).

EXAMPLES

Example 1—Maltodextrin Modification with nOSA (DS 0.1, 0.3, 0.5, 0.7)

(b) A maltodextrin (C*Dry MD 01915, Cargill, 500 g on dry basis, Mw of about 20,000 Daltons, PDI of between 10 and 20, DE of about 18) was suspended and dissolved in water at room temperature to form a slurry. The slurry was stirred during the entire reaction with an overhead stirrer. First the pH was brought to 8.5 with an 8% w/w NaOH solution. nOSA reagent (229.05 g) was added slowly (30 min) with a pump while maintaining the pH between 8 and 8.5 (with a pH controlled pump). After the nOSA addition reaction continued for 90 min under pH control at room temperature the addition of NaOH addition was stopped. In total 594 g of NaOH solution was consumed during the reacting, resulting in a DS of 0.32 (reaction efficiency 90.9%).

(c) A maltodextrin (C*Dry MD 01915, Cargill, 500 g on dry basis) was suspended and dissolved in water at room temperature to form a slurry. The slurry was stirred during the entire reaction with an overhead stirrer. First the pH was brought to 8.5 with an 8% w/w NaOH solution. nOSA reagent (534.45 g) was added slowly (120 min) with a pump while maintaining the pH between 8 and 8.5 (with a pH controlled pump). After the nOSA addition reaction continued for 30 min under pH control at room temperature the addition of NaOH addition was stopped. In total 1477.7 g of NaOH solution was consumed during the reacting, resulting in a DS of 0.69 (reaction efficiency 83.7%).

(a) The procedure was repeated, with the difference that the amount of nOSA reagent was adjusted to result in a modified dextrin having a DS of 0.1

(d) The procedure was repeated, with the difference that the amount of nOSA reagent was adjusted to result in a modified dextrin having a DS of 0.5

Example 2—Starch Modification with nOSA (DS 0.1, 0.3, 0.5, 0.7)

The procedure of Example 1 was repeated with C*iCoat 07520 (Mw of about 75 kDaltons, DE of between 4 and 6) as the starting material and appropriate amount of nOSA reagent to create Examples 2(a) DS 0.1; 2(b) DS 0.3; 2(c) DS 0.5; and 2(d) DS 0.7.

Example 3—Dextrin Modification with nOSA (DS 0.1, 0.3, 0.5, 0.7)

(b) First a paste of a corn dextrin (C*Film 07325, Cargill, Mw of about 35.800 Daltons, PDI of about 5.5, DE of between 0 and 2) was used to make a 10 wt % slurry of said dextrin in water. The slurry was cooked in a Brabender having the following temperature program: start temperature 50° C., maximum temperature 90° C. (20 min hold), end temperature 50° C. The heating/cooling time was 1.5° C./min and the rotation speed 75/min. The dry solid content of the paste was measured and adapted to the required dry solid content (30 wt %) by adding water at room temperature and stirred to homogenize with an overhead stirrer. 600 g on dry basis of the adjusted paste was taken. The paste was stirred during the entire reaction with an overhead stirrer. First the pH was brought to 8.5 with an 8% w/w NaOH solution. nOSA reagent (274.86 g) was added slowly (80 min) with a pump while maintaining the pH between 8 and 8.5 (using a pH controlled pump) with an 8% w/w NaOH solution. After that nOSA addition reaction continued for the next 40 min under pH control at room temperature after which the NaOH addition was stopped. In total 724 g of NaOH solution was consumed during the reacting, resulting in a DS of 0.31 (reaction efficiency 89.23%).

(c) The procedure was repeated, with the difference that the amount of nOSA reagent was adjusted to result in a modified dextrin having a DS of 0.7.

(a) The procedure was repeated, with the difference that the amount of nOSA reagent was adjusted to result in a modified dextrin having a DS of 0.1.

(d) The procedure was repeated, with the difference that the amount of nOSA reagent was adjusted to result in a modified dextrin having a DS of 0.5.

Example 4—Starch Modification with nOSA (DS 0.1, 0.3, 0.5, 0.7)

The procedure of Example 1 was repeated with C*07302 (Mw of about 400 kDaltons, DE of between 2-4, as the starting material and appropriate amount of nOSA reagent to create Examples 2(a) DS 0.1; 2(b) DS 0.3; 2(c) DS 0.5; and 2(d) DS 0.7.

Example 5

TABLE 1

| Raw Materials | DS | Foam Volume Stability (vs time-minutes) | | | | |
|---|---|---|---|---|---|---|
| | | T = 0 | T = 1 | T = 2 | T = 3 | T = 4 |
| Example 1 | 0 | 29 | 29 | 29 | 29 | 29 |
| (a) | 0.1 | 45 | 43 | 42 | 40 | 40 |
| (b) | 0.3 | 57 | 55 | 53 | 53 | 53 |
| (c) | 0.5 | 58 | 57 | 54 | 53 | 53 |
| (d) | 0.7 | 60 | 58 | 55 | 54 | 54 |
| Example 2 | 0 | | | | | 29 |
| (a) | 0.1 | 29 | 27 | 27 | 27 | 27 |
| (b) | 0.3 | 35 | 33 | 32 | 32 | 32 |
| (c) | 0.5 | 50 | 46 | 45 | 43 | 42 |
| (d) | 0.7 | 42 | 41 | 39 | 38 | 38 |
| Example 3 | 0 | | | | | 29 |
| (a) | 0.1 | 28 | 27 | 27 | 27 | 27 |
| (b) | 0.3 | 45 | 43 | 42 | 40 | 35 |
| (c) | 0.5 | 45 | 43 | 43 | 43 | 43 |
| (d) | 0.7 | 43 | 43 | 43 | 43 | 43 |
| Example 4 | 0 | | | | | 29 |
| (a) | 0.1 | 29 | | | | 29 |
| (b) | 0.3 | 34 | 33 | 32 | 32 | 32 |
| (c) | 0.5 | 40 | 37 | 37 | 35 | 35 |
| (d) | 0.7 | 41 | 38 | 38 | 38 | 38 |
| CAPB | 0 | 65 | 65 | 62 | 60 | 59 |
| nOSA reagent | | 29 | 29 | 29 | 29 | 29 |

Stability

To test the stability of foam in products containing the anhydride modified starches of the present disclosure a model shampoo system was utilized. Stability is evaluated visually by observing the stability of the foam over time. A 1% by weight solution of test anhydride modified starch was prepared in demi-water. 30 milliliters of the test solution was added to a 100 ml graduated cylinder. The cylinder was shaken 10 times and the volume of foam recorded immediately and then at 1, 2, 3, and 4 minutes from the end of shaking. The foam fails as it begins to settle or collapse. For some uses it is highly desirable for the foam to be stable over an extended period of time. In most examples, the foam maintained 80% or greater of its initial height after 4 minutes of observation.

TABLE A

Example for Sulphate Shampoo formulation.

| Phase | Trade name | INCI name | % Active Mater | % WT | Phase |
|---|---|---|---|---|---|
| A1 | Demi. water | Aqua | Qs to 100% | 52.40% | A1 |
| A2 | Iscaguard PEHG | Phenoxyethanol (and) Ethylhexylglycerin | 1.0%* | 1.00% | A2 |
| A3 | Actigum CS11 QD | Sclerotium Gum | 0.3% | 0.30% | A3 |
| B1 | Tensagex EOC628BV | Sodium Laureth Sulfate | 4.26% | 16.00% | B1 |
| B2 | Pureact Gluco C | Coco-Glucoside | 3.08% | 6.00% | B2 |
| B3 | Empigen BS/FA | Cocamidopropyl Betaine | 4.31% | 14.00% | B3 |
| C | Jaguar Excel | Guar Hydroxypropyltrimonium Chloride | 0.2% | 10.20% (water 10%, 0.2% Cationic guar) | C |
| D | pH adjuster | | qs | qs | D |

*using 1.0% weight of solution Iscaguard PEHG

Example 6 to 16 have been prepared as follow: In a beaker (800 g) prepare phase A, add A1 then A2. Mix @ 600 RPM with Ika marine propeller until homogenous. With an ultra Thurax 25, sprinkle A3 @ 10000 RPM into phase A and let it mix for 10 minutes. Add slowly ingredients of phase B, into phase A, one by one @ 300-400 RPM with Ika propeller blade. Wait 5-10 minutes between each addition until homogenous. Prepare Phase C in a small beaker using defloculeuse from Ika to disperse well the powder (600-800 RPM or vortex for 15 min). The phase should be homogenous. Adjust pH around 5 with citric acid. Add Phase C slowly to AB (800-1000 RPM) for 10 min until homogenous.

The Surfactant phase has been either partially or fully replaced by the invention using each time the full formulation as illustrated in Table A.

Examples: Showing surfactants only, from the full formulation is in Table A.

Example 6: SULFATE SHAMPOO control

| Trade name | INCI name | Supplier | % Active Mater as ingredients are sold as solutions. | % WT | % Dry Mater in Final Formulation |
|---|---|---|---|---|---|
| Tensagex E0C628BV | Sodium Laureth Sulfate | Tensachem | 26.6% | 16.00% | 4.26% |
| Pureact Gluco C | Coco-Glucoside | Innospec | 51.4% | 6.00% | 3.08% |
| Empigen BS/FA | Cocamidopropyl Betaine | Innospec | 30.8% | 14.00% | 4.31% |

Example 7: SULFATE SHAMPOO - All Anionic surfactant replaced by invention

| Trade name | INCI name | Supplier | % Active Mater | % WT | % Dry Mater |
|---|---|---|---|---|---|
| TENSAGEX E0C628BV | Sodium Laureth Sulfate | Tensachem | 26.6% | 0% | 0% |
| Pureact Gluco C | Coco-Glucoside | Innospec | 51.4% | 6.00% | 3.08% |
| Empigen BS/FA | Cocamidopropyl Betaine | Innospec | 30.8% | 14.00% | 4.31% |
| Modified Starch of Example 1 | Sodium starch octenylsuccinate | Cargill | 32.1% | 13.27% | 4.26% |

Example 8: SULFATE SHAMPOO - All Non-Ionic surfactant replaced by invention

| Trade name | INCI name | Supplier | % Active Mater | % WT | % Dry Mater |
|---|---|---|---|---|---|
| TENSAGEX E0C628BV | Sodium Laureth Sulfate | Tensachem | 26.6% | 16.00% | 4.26% |
| Pureact Gluco C | Coco-Glucoside | Innospec | 51.4% | 0.00% | 0.00% |
| Empigen BS/FA | Cocamidopropyl Betaine | Innospec | 30.8% | 14.00% | 4.31% |
| Modified Starch of Example 1 | Sodium starch octenylsuccinate | Cargill | 32.1% | 9.60% | 3.08% |

Example 9: SULFATE SHAMPOO - All Amphoteric surfactant replaced by invention

| Trade name | INCI name | Supplier | % Active Mater | % WT | % Dry Mater |
|---|---|---|---|---|---|
| TENSAGEX E0C628BV | Sodium Laureth Sulfate | Tensachem | 26.6% | 16.00% | 4.26% |
| Pureact Gluco C | Coco-Glucoside | Innospec | 51.4% | 6.00% | 3.08% |
| Empigen BS/FA | Cocamidopropyl Betaine | Innospec | 30.8% | 0.00% | 0.00% |
| Modified Starch of Example 1 | Sodium starch octenylsuccinate | Cargill | 32.1% | 13.42% | 4.31% |

Example 10: SULFATE SHAMPOO - Half of total active all each surfactants (11.65% divide by 2 equal 5.825%) - replaced by the invention

| Trade name | INCI name | Supplier | % Active Mater | % WT | % Dry Mater |
|---|---|---|---|---|---|
| TENSAGEX E0C628BV | Sodium Laureth Sulfate | Tensachem | 26.6% | 8.00% | 2.13% |
| Pureact Gluco C | Coco-Glucoside | Innospec | 51.4% | 3.00% | 1.54% |
| Empigen BS/FA | Cocamidopropyl Betaine | Innospec | 30.8% | 7.00% | 2.15% |
| Modified Starch of Example 1 | Sodium starch octenylsuccinate | Cargill | 32.1% | 18.13% | 5.82% |

Example 11: SULFATE SHAMPOO - Half of total active all each surfactants (11.65% divide by 2 equal 5.825%) - replaced by the invention - Example 3

| Trade name | INCI name | Supplier | % Active Mater | % WT | % Dry Mater |
|---|---|---|---|---|---|
| TENSAGEX E0C628BV | Sodium Laureth Sulfate | Tensachem | 26.6% | 8.00% | 2.13% |
| Pureact Gluco C | Coco-Glucoside | Innospec | 51.4% | 3.00% | 1.54% |
| Empigen BS/FA | Cocamidopropyl Betaine | Innospec | 30.8% | 7.00% | 2.15% |
| Modified Starch of Example 3 | Sodium starch octenylsuccinate | Cargill | 32.1% | 18.13% | 5.82% |

Example 12: SULFATE SHAMPOO - all surfactants (11.65%) - replaced by the invention

| Trade name | INCI name | Supplier | % Active Mater | % WT | % Dry Mater |
|---|---|---|---|---|---|
| TENSAGEX E0C628BV | Sodium Laureth Sulfate | Tensachem | 26.6% | 0% | 0% |
| Pureact Gluco C | Coco-Glucoside | Innospec | 51.4% | 0% | 0% |
| Empigen BS/FA | Cocamidopropyl Betaine | Innospec | 30.8% | 0% | 0% |
| Modified Starch of Example 1 | Sodium starch octenylsuccinate | Cargill | 32.1% | 36.26% | 11.65% |

All examples 6 to 12 are stable shampoo formulations (4 weeks at 45° C. Celsius). All examples 6 to 10 and 12 are fully transparent formulae and with good foaming properties expressed either by using the 1% active dilution cylinder method or by forming the lather from washing with real Hair switches. By good foaming properties, it is meant to be both lather quantity (lather volume) and lather quality (lather stability overtime and small bubble size). Sample 11 made with Modified Starch of Example 3 is not transparent.

TABLE B

| | | Example for Sulphate free Shampoo formulation | | |
|---|---|---|---|---|
| Phase | Trade name | INCI name | % Active Mater | % Dry Mater |
| A1 | Demi. water | Aqua | Qs to 100% | Qs to 100% |
| A2 | Iscaguard PEHG | Phenoxyethanol (and) Ethylhexylglycerin | 1.0%* | 1.00% |
| A3 | Actigum CS11 QD | Sclerotium Gum | 0.3% | 0.30% |
| B1 | Pureact I-85 C | Sodium Cocoyl Isethionate | 82.30% | 1.80% |
| B2 | Iselux LQ CLR SB | Sodium Lauroyl Methyl Isethionate | 33.50% | 18.00% |
| B3 | Empigen BS/FA | Cocamidopropyl Betaine | 30.80% | 11.67% |
| C | Jaguar Excel | Guar Hydroxypropyltrimonium Chloride | 0.2% | 0.2% |
| D | pH adjuster | | qs | qs |

The Surfactant phase has been either partially or fully replaced by the invention using each time the full formulation as illustrated in Table B:

Examples Showing sulphate free surfactants only, from the full formulation is in (Table B).

Example '13: SULFATE FREE SHAMPOO control

| Trade name | INCI name | Supplier | % Active Mater | % WT | % Dry Mater |
|---|---|---|---|---|---|
| Pureact I-85 C | Sodium Cocoyl Isethionate | Innospec | 82.3% | 1.80% | 1.48% |
| Iselux LQ CLR SB | Sodium Lauroyl Methyl Isethionate | Innospec | 33.5% | 18.00% | 6.03% |
| Empigen BS/FA | Cocamidopropyl Betaine | Innospec | 30.8% | 11.67% | 3.59% |

Example 14: SULFATE FREE SHAMPOO - All both Anionic surfactants replaced by the invention

| Trade name | INCI name | Supplier | % Active Mater | % WT | % Active Mater |
|---|---|---|---|---|---|
| Pureact I-85 C | Sodium Cocoyl Isethionate | Innospec | 82.3% | 0% | 0% |
| Iselux LQ CLR SB | Sodium Lauroyl Methyl Isethionate | Innospec | 33.5% | 0% | 0% |
| Empigen BS/FA | Cocamidopropyl Betaine | Innospec | 30.8% | 11.67% | 3.59% |
| Modified Starch of Example 1 | Sodium starch octenylsuccinate | Cargill | 32.0% | 23.47% | 7.51% |

Example 15: SULFATE FREE SHAMPOO - All Amphoteric surfactant replaced by the Invention

| Trade name | INCI name | Supplier | % Active Mater | % WT | % Dry Mater |
|---|---|---|---|---|---|
| Pureact I-85 C | Sodium Cocoyl Isethionate | Innospec | 82.3% | 1.80% | 1.48% |
| Iselux LQ CLR SB | Sodium Lauroyl Methyl Isethionate | Innospec | 33.5% | 18.00% | 6.03% |
| Empigen BS/FA | Cocamidopropyl Betaine | Innospec | 30.8% | 0% | 0% |
| Modified Starch of Example 1 | Sodium starch octenylsuccinate | Cargill | 32.0% | 11.23% | 3.59% |

Example 16: SULFATE FREE SHAMPOO - Half of total active (11.11% divided by 2 equal 5.55%) replaced by Invention

| Trade name | INCI name | Supplier | % Active Matter | % WT | % Active Matter |
|---|---|---|---|---|---|
| Pureact I-85 C | Sodium Cocoyl Isethionate | Innospec | 82.3% | 0.90% | 0.74% |
| Iselux LQ CLR SB | Sodium Lauroyl Methyl Isethionate | Innospec | 33.5% | 9.00% | 3.02% |
| Empigen BS/FA | Cocamidopropyl Betaine | Innospec | 30.8% | 5.84% | 1.80% |
| Modified Starch of Example 1 | Sodium starch octenylsuccinate | Cargill | 32.0% | 17.20% | 5.50% |

Example 17: SULFATE FREE SHAMPOO - All surfactants replaced by the invention

| Trade name | INCI name | Supplier | % Active Matter | % WT | % Dry Matter |
|---|---|---|---|---|---|
| Pureact I-85 C | Sodium Cocoyl Isethionate | Innospec | 82.3% | 0.90% | 0.74% |
| Iselux LQ CLR SB | Sodium Lauroyl Methyl Isethionate | Innospec | 33.5% | 9.00% | 3.02% |
| Empigen BS/FA | Cocamidopropyl Betaine | Innospec | 30.8% | 5.84% | 1.80% |
| Modified Starch of Example 1 | Sodium starch octenylsuccinate | Cargill | 32.0% | 34.4% | 11.11% |

All examples 6 to 17 are stable shampoo formulations (4 weeks at 45° C. Celsius). All examples 6 to 10 and 12 to 17 are fully transparent formulae.

Example 14 to 17 formulae display good foaming properties were seen either by using the 1% active dilution cylinder method or by forming the lather from washing with real Hair switches. By good foaming properties, it is meant to be both lather quantity (lather volume) and lather quality (lather stability over time and small bubble size).

All shampoo formulation can be used—as is—or tuned with typical skin care body wash ingredient to be used as in shower or bath body cleanser or body washes.

Foam Development

To test the ability of a formulation containing the anhydride modified starch to develop of foam a profusion test was utilized. Into a long neck beaker, 100 gr of a solution containing 1% ds of the test material is carefully poured to avoid turbulence. After resting, the paddle of a bench mixer Turbotest® is submerged, rotor turned on, and a vortex is formed. From the starting rotor, time is noted until the top surface is flat and vortex is not visible anymore. This is considered the profusion time. Examples 6-10 and 13-17 were evaluated in the profusion test and surprisingly, the substitution of single surfactants or half of all the surfactants from standard sulfate and sulfate-free shampoo formulations by the anhydride modified starch of the present invention did not significantly affect profusion time. Therefore, the shampoo formulations containing the anhydride modified starches disclosed herein have the same ability to build foam as standard products.

Additional personal care application of the invention can be in Soap bar form; as illustrated in the Example 18.

Example 18: Soap Bar

| | Trade name | INCI name | Supplier | % Active Matter | % WT | % Dry Matter |
|---|---|---|---|---|---|---|
| C1 | Pureact I-85 C | Sodium Cocoyl Isothionate | Innospec | 82.3% | 6.075% | 5% |
| A1 | Agri-Pure ™ AP-80 | Helianthus annuus (sunflower) seed oil | Cargill | 100% | 30% | 30% |
| A2 | Agri-Pure ™ AP-20 | Cocos nucifera (coconut) oil | Cargill | 100% | 20% | 20% |
| B2 | Water | Aqua | — | 100% | qs to 100% | qs to 100% |
| B1 | NaOH | Sodium Hydroxyde | — | 50% | 14.6%** | 7.3%** |
| C2 | C*Cream Gel 70001 | Native Tapioca Starch | Cargill | 100% | 6% | 6% |
| C3 | C*EmTex ™ 06328 | Sodium starch octenylsuccinate | Cargill | 100% | 4% | 4% |
| C4 | Modified Starch of Example 1 Or Modified Starch of Example 3 | Sodium starch octenylsuccinate | Cargill | 32.0% | 15.625% | 5% |

**NaOH desired quantity level will depend on the saponification values & proportions of the oils types used; the level of NaOH as well as the level of other ingredients will be tuneable to fit with the desired sensorial and performance properties of the soap (harder, medium or softer textures & appearance, foaming/cleaning properties).

In Example 18, The soap was made by heating first all oils A1 and A2 to approx. 70° C. and mixed well using IKA laboratory reactor. NaOH B1 and water B2 are added slowly to mix A1+A2 and maintaining mixing for 30 minutes. Temperature was controlled to not exceed 80-85° C. Subsequently, Surfactant C1 and Starches C2, C3 were added to main mix followed by C4 the invention. Homogenization at 5000 rpm for 10 minutes, then the final mix was placed in individual molds and allowed to cool.

We claim:

1. An anhydride modified dextrin wherein the anhydride modified dextrin has (i) an anhydride modification comprising a degree of substitution between 0.1 and 0.8 and (ii) was prepared from a base dextrin having an average molecular weight of between 15,000 and 200,000 g/mol, and wherein the anhydride modification includes a hydrophobic moiety including 8 to 22 carbon atoms such that the anhydride modified dextrin has a surfactant functionality and in an effective amount to build foam.

2. The anhydride modified starch of claim 1, wherein the anhydride modified dextrin is an n-octenyl succinate anhydride (nOSA) modified dextrin starch.

3. The anhydride modified starch of claim 2, wherein the degree of substitution is between 0.2 and 0.5.

4. The anhydride modified starch of claim 3, wherein the base dextrin has an average molecular weight of between 15,000 and 50,000 g/mol.

5. A personal care or home care formulation comprising an anhydride modified dextrin functioning in the formulation as a surfactant, wherein the anhydride modified dextrin has (i) an anhydride modification comprising a degree of substitution between 0.1 and 0.8 and (ii) was prepared from a base dextrin having an average molecular weight of between 15,000 and 200,000 g/mol, and wherein the anhydride modification includes a hydrophobic moiety having 8 to 22 carbon atoms and in an effective amount to build foam.

6. The personal care or home care formulation of claim 5, wherein the formulation is selected from the group consisting of shampoo, sulphate free shampoo, hair conditioner, hair leave-on, body wash, skin cleanser, hair cleanser, bar soap, toothpaste, and mouthwash.

7. The personal care or home care formulation of claim 6, wherein the anhydride modified dextrin is an nOSA modified dextrin.

8. The personal care or home care formulation of claim 7, wherein the degree of substitution is between 0.2 and 0.5.

9. The personal care or home care formulation of claim 8, wherein the base dextrin has an average molecular weight of between 15,000 and 50,000 g/mol.

10. The personal care or home care formulation of claim 6, wherein the formulation comprises between 0.1% and 50%, 1% to 25%, or 1% to 15% anhydride modified dextrin by weight.

11. The personal care or home care formulation of claim 8, wherein the formulation is a shampoo, sulfate-free shampoo, hair conditioner, hair leave-on, or bodywash.

12. The personal care or home care formulation of claim 5, wherein the formulation is selected from the group consisting of a hair mask and a facial cleanser.

13. The personal care or home care formulation of claim 5, wherein the anhydride modification includes a hydrophobic moiety having 8 to 18 carbon atoms.

14. The personal care or home care formulation of claim 5, wherein the base dextrin is a cyclodextrin.

15. The personal care or home care formulation of claim 5, wherein the base dextrin is a maltodextrin.

16. The personal care or home care formulation of claim 5, wherein the base dextrin is a pyrodextrin.

17. The personal care or home care formulation of claim 5, wherein the base dextrin has an amylose content of 1 to 25 weight percent.

18. The personal care or home care formulation of claim 5, wherein the base dextrin has an amylopectin content of 75 to 95 weight percent.

19. The personal care or home care formulation of claim 5, wherein the base dextrin has an average molecular weight in the range from 15,000 to 50,000 g/mol.

* * * * *

UNITED STATES PATENT AND TRADEMARK OFFICE
CERTIFICATE OF CORRECTION

PATENT NO. : 12,391,772 B2
APPLICATION NO. : 17/753655
DATED : August 19, 2025
INVENTOR(S) : Stéphane Biltresse et al.

It is certified that error appears in the above-identified patent and that said Letters Patent is hereby corrected as shown below:

In the Specification

In Column 2, Line 54 delete "lauyl" and insert -- lauryl --, therefor.
In Column 2, Line 54 delete "cocyl" and insert -- cocoyl --, therefor.
In Column 2, Line 54 delete "cocyl" and insert -- cocoyl --, therefor.
In Column 9, Line 32 delete "1-50% 1-30%" and insert -- 1-50%, 1-30%, --, therefor.
In Column 10, Line 48 delete "Sample" and insert -- (Sample --, therefor.
In Column 11, Line 8 delete "(DS)" and insert -- (DSC) --, therefor.
In Column 11, Line 47 delete "0.1" and insert -- 0.1. --, therefor.
In Column 11, Line 50 delete "0.5" and insert -- 0.5. --, therefor.

Signed and Sealed this
Eighteenth Day of November, 2025

John A. Squires
*Director of the United States Patent and Trademark Office*